United States Patent [19]

Bergfeld et al.

[11] Patent Number: 4,898,978
[45] Date of Patent: Feb. 6, 1990

[54] PROCESS FOR THE PREPARATION OF N,N'-DISUBSTITUTED GUANIDINES

[75] Inventors: Manfred Bergfeld, Erlenbach-Mechenhard; Ludwig Eisenhuth, Obernburg; Hans Zengel, Kleinwallstadt, all of Fed. Rep. of Germany

[73] Assignee: Akzo N.V., Arnhem, Netherlands

[21] Appl. No.: 819,881

[22] Filed: Jan. 17, 1986

[30] Foreign Application Priority Data

Jan. 17, 1985 [DE] Fed. Rep. of Germany ....... 3501383

[51] Int. Cl.$^4$ ........................................... C07C 128/00
[52] U.S. Cl. .................................................... 564/231
[58] Field of Search ......................................... 564/231

[56] References Cited

U.S. PATENT DOCUMENTS 1,630,769  5/1927  Scott .................................... 564/231

FOREIGN PATENT DOCUMENTS

| 418100 | 8/1925 | Fed. Rep. of Germany | 564/231 |
| 418994 | 9/1925 | Fed. Rep. of Germany | 564/231 |
| 630966 | 6/1936 | Fed. Rep. of Germany | 564/231 |
| 632130 | 7/1936 | Fed. Rep. of Germany | 564/231 |
| 2154721 | 5/1973 | Fed. Rep. of Germany | 564/231 |
| 2716897 | 1/1980 | Fed. Rep. of Germany | |
| 303044 | 12/1928 | United Kingdom | 564/231 |

OTHER PUBLICATIONS

Chemical Abstract 92:94093g, Hungarian Teljes 17.165.
Chemical Abstract 99:212248f.
Noncondensed Aromatic Compounds, vol. 63, p. 35, Col. 1734, "Diphenyguanidine".
W. Theieheimer, "Synthetic Methods", vol. 25 (1971), No. 323.
Ullmanns Encyclopedia, Fourth Edition, vol. 12, pp. 416, 417 and 420.

*Primary Examiner*—James H. Reamer
*Attorney, Agent, or Firm*—Oliff & Berridge

[57] ABSTRACT

A process for the preparation of aromatic N,N'-disubstituted guanidines is described in which the corresponding aromatic N,N'-disubstituted thioureas are reacted with ammonia and oxygen or with an oxygen-containing gas, in the presence of a solvent and elements acting as catalysts having atomic numbers 21 through 30 in the Periodic Table or the lanthanides or the salts, oxides or complexes thereof.

11 Claims, No Drawings

PROCESS FOR THE PREPARATION OF N,N'-DISUBSTITUTED GUANIDINES

BACKGROUND OF THE INVENTION

The present invention relates to a process for the preparation of N,N'-disubstituted guanidines from the corresponding N,N'-disubstituted thioureas and ammonia.

Substituted guanidines find wide application especially as vulcanization accelerators; the most important representatives being N,N'-diphenylguanidine (I; DPG) and di-o-tolylguanidine (II; DOTG):

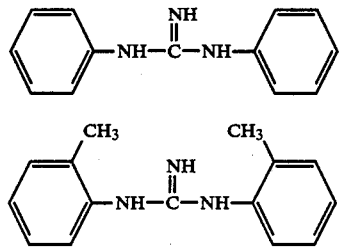

Both products are synthesized on an industrial scale by reacting aniline with cyanogen chloride. This proceeds via the following stages:

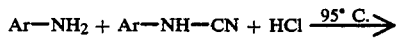

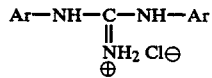

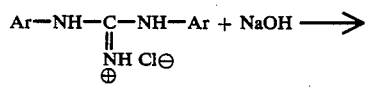

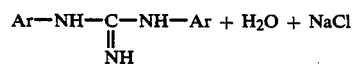

After the last stage of the reaction, removal of aniline by means of steam, purification with activated charcoal and sodium sulfite, filtration and, finally, precipitation with sodium hydroxide solution are necessary. This process is described in ULLMANNS ENCYCLOPEDIA, 4th edition, Vol. 12, page 416.

The major disadvantages of this process are the above-mentioned processing and purification steps and the use of the highly poisonous cyanogen chloride. In addition, the latter compound must first be synthesized by a preceeding reaction from chlorine and sodium cyanide (a more recent method of manufacturing cyanogen chloride starts with chlorine and hydrogen cyanide; Unexamined West German Application DE-OS 21 54 721).

The synthesis of N,N'-disubstituted guanidines by reaction of the corresponding N,N'-disubstituted thioureas with ammonia is also known in the art. For example, West German Patents DE-PS 418,100, 481,994, 630,966, and 632,130 describe processes in which the thioureas and ammonia are reacted with lead monoxide, zinc oxide, or lead salts, e.g., according to the following equation:

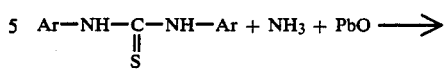

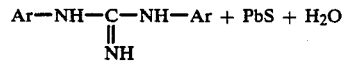

However, these reactions proceed very slowly and are incomplete. In addition, reaction mixtures of guanidine, the starting thiourea, lead monoxide and lead sulfide, as well as other by-products are formed, which are very difficult to separate. A complete reaction can be achieved only if the lead monoxide is used in great excess.

The Hungarian Teljes 17.165 also discloses a process for synthesizing N,N'-diphenylguanidine by reacting N,N'-diphenylthiourea and ammonia in an organic solvent with lead or zinc oxide, hydroxide, oxyhydroxide, etc., and 1 to 10 weight % sulfur catalyst.

Soviet Union patent 168,683 discloses a process for synthesizing diphenylguanidine by reacting diphenylthiourea and ammonia in the presence of an oxidation agent, such as, for example, sodium or potassium bichromate or manganese peroxide. Thus, according to these known processes, heavy metal oxygen compounds are used which participate stoichiometrically in the chemical reaction. By-products of the reaction include heavy metal oxides, sulfides and sulphur oxidation products, so that here, too, a complicated process for isolating the product must be carried out. Yields of diphenylguanidine in the above process are less than 90%.

SUMMARY OF THE INVENTION

The present invention has as its object cost-effective process for preparing N,N'-disubstituted guanidines, which does not have the above-mentioned disadvantages.

The above object is achieved by a process for the preparation of N,N'-disubstituted guanidines having the general formula:

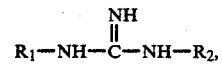

wherein $R_1$ and $R_2$ may be the same or different and may represent an unsubstituted or a mono- or polysubstituted aromatic group, comprising the reaction of corresponding N,N'-disubstituted thioureas with ammonia and oxygen, or with an oxygen-containing gas, in the presence of a solvent and elements having atomic numbers 21 through 30 in the Periodic Table, or the lanthanides or the salts, oxides, or complexes thereof acting as catalysts.

DETAILED DESCRIPTION OF THE INVENTION

Depending on the reaction conditions, the novel process can be based on the following overall equations:

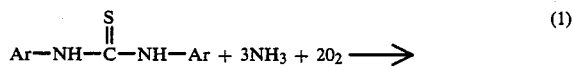

(1)

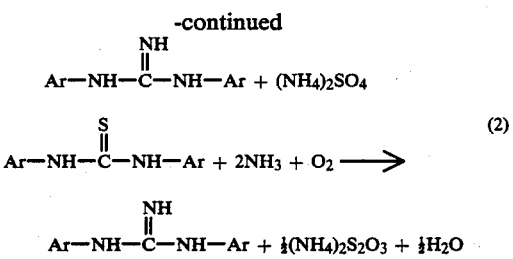

As is apparent from the above equations, readily available starting materials that can be handled with ease are employed. In addition to the formation of diarylguanidines, ammonium sulfate is formed, if an aqueous solution is used, and ammonium thiosulfate is formed, if organic solvents are used.

The N,N'-disubstituted thioureas to be used according to the invention can be synthesized in a known and simple manner from readily available starting products. For example, according to the process disclosed in Accepted West German Patent Application DE-AS 2,716,897 carbon disulfide and aromatic amine are reacted in an aqueous solution, with a high resultant yield.

The aromatic amines used in the synthesis of the required N,N'-disubstituted thioureas are amines with the general formula $RNH_2$, where R may represent an unsubstituted or a mono- or polysubstituted phenyl group or naphthyl group, in which the substituents may be an alkyl and/or alkoxy group having 1 to 6 carbon atoms, a cycloalkyl, phenyl, phenylether, or benzyl group, a nitro group and/or a chlorine atom. Preferred aromatic amines are aniline, o-, m-, and p-toluidine, o-, m-, and p-ethylaniline, o-, m-, and p-isopropylaniline, p-tert-butylaniline, 2,4-dimethylaniline, 2-methyl-6-ethylaniline, o-, m-, and p-methoxyaniline, o-, m-, and p-chloroaniline, p-nitroaniline, p-phenylaniline, 4-aminodiphenyl ether, 1- and 2-aminonaphthalene, 2-, 3-, 4-, and 7-methyl-1-amino-naphthalene and 1- and 6-methyl-2-aminonaphthalene.

Especially preferred starting compounds for the novel process of the invention are N,N'-diphenylthiourea and N,N'-di-o-tolylthiourea.

To carry out the novel process of the invention, the specific thiourea, the ammonia, and the catalyst are first dissolved or suspended in a solvent and treated with oxygen. The oxygen required for the reaction is taken up from the reaction mixture. It is also possible to add the thiourea to the reaction mixture during the reaction. In many instances, it is beneficial to add separately the ammonia utilized by the reaction. In this case, the synthesized guanadine appears mostly as a sediment and subsequently can be filtered off. In other instances, the desired end product is obtained by cooling or evaporation of the reaction mixture.

Finally, a very pure final product requiring no further purification is obtained in high yields and selectivity. As a rule, it is advantageous to let the catalyst as well as the by-products of ammonium sulfate or thiosulfate remain dissolved in the mother liquor. Preferably, the mother liquor of the process is circulated in additional commercial applications.

A surprising feature of the novel process is that a pure product is obtained from these readily available starting materials, that can be handled with ease, has high yield and selectivity and is a result of a simple reaction sequence which avoids costly processing steps. Therefore, the process of the invention is eminently suitable for a cost-effective production of aromatic N,N'-disubstituted guanidines.

The amount of ammonia used can be varied over a wide range. However, the ammonia should be present in the reaction mixture at least somewhat in molar excess to the amount of thiourea used, i.e., preferably at least 2 moles of ammonia per mole of thiourea. If an aqueous solution is employed, at least 3 moles of ammonia per mole of thiourea is preferred. Especially preferred is the use of at least 5 moles of ammonia per mole of thiourea. An increase in the amount of ammonia accelerates the reaction.

Solutions with a very high ammonia content may also be used. The upper limit of ammonia is determined by the solubility of the ammonia in the particular solvent and therefore by the particular pressure applied and the particular reaction temperature.

All solvents which are inert to the starting and end products and to oxygen may be used as solvents. Preferred solvents are water and/or organic solvents. Preferred organic solvents are alcohols, especially those having 1 to 4 carbon atoms.

According to the invention, the catalysts may be used in elemental form, i.e., in metallic form, e.g., as a metal powder, such as copper powder. The catalyst may consist of a single element. Mixtures or alloys may also be employed.

Elements having the atomic numbers 21 to 30 as well as the lanthanides may also be used as catalysts. The elements or lanthanides are utilized in the form of chemical compounds, namely the salts, oxides or complexes of the elements or lanthanides, both individually and as mixtures. Examples of the above are copper acetate, copper chloride, copper oxide, copper sulfate, manganese acetate, cobalt acetate, cerous nitrate, and iron sulfate.

The catalysts used in the manner taught by the invention are effective in very small amounts. For example, about 0.003 mmol per mole of thiourea is sufficient. Especially preferred, however, are amounts of at least 0.01, especially 0.025 mmol of catalysts per mole of thiourea.

The process of the invention can be carried out at temperatures starting at about 0° C. Preferred temperatures are in the range of 20° to 100° C. Lower temperatures involve longer reaction times, while higher temperatures entail the risk of a decline in selectivity.

In general, oxygen pressures or partial oxygen pressures of at least 0.1 bar are employed according to the invention. As expected, the reaction rate increases with increasing pressure. A pressure range of 0.1 to 10 bar is preferred for reasons of economy and safety.

The invention will now be described with reference to the following applications:

EXAMPLE 1

A suspension of 22.8 g (0.1 mol) of diphenylthiourea, 140 g of a 25 weight-percent solution of ammonia (2.21 mol) in a mixture of 80 parts by weight of water and 20 parts by weight of ethanol and 20 mg (0.1 mmol) of copper II acetate $Cu(OAc)_2$ are reacted at a temperature of 50° C. and a partial oxygen pressure of 4 to 5 bar for 7 hours.

20.5 g of diphenylguanidine (97% of the theoretical) precipitates as a white sediment with a melting point of 146°–147° C. This product has a 98% purity.

EXAMPLE 2

A suspension of 19.2 g (0.075 mol) of di-o-tolylthiourea, 180 g of a 35 weight percent solution of ammonia (3.7 mol) in water, and 20 mg (0.1 mmol) of $Cu(OAc)_2$ are reacted at a temperature of 65° C. and a partial oxygen pressure of 2 to 3 bar for 4 hours.

17.7 g of di-o-tolylguanidine (98.8% of the theoretical) precipitates as a white sediment with a melting point of 172°-174° C. This product has a 98.2% purity.

EXAMPLE 3

A reaction mixture of 22.8 g (0.1 mol) of diphenylthiourea, 45 g (2.65 mol) of ammonia, and 85 g of water is caused to react in the presence of 0.1 mmol of $Cu(OAc)_2$ catalyst with oxygen during active agitation. The reaction temperature is 50° C., oxygen pressure 3 bar, and the reaction time 6 hours. The white sediment is filtered off, washed, and dried: 20.8 g of diphenylguanidine corresponds to 98.4% of the theoretical. Product purity is assessed as 98%. The mother liquor contains primarily ammonium sulfate.

EXAMPLE 4

A reaction mixture consisting of 0.2 mol of diphenylthiourea, 2.6 mol of ammonia, 75 g of water, and 75 g of methanol is reacted in the presence of 0.05 mmol of $Cu(OAc)_2$ with oxygen. The reaction temperature is 50° C., the oxygen pressure 1 bar, and the reaction time 60 min. The white, finely crystalline sediment is filtered off, washed, and dried and represents 39.6 g of diphenylguanidine. Another 1.8 g of diphenylguanidine is dissolved in the mother liquor. Accordingly, the total yield of diphenylguanidine is 41.4 g, which corresponds to 98.1% of the theoretical. The mother liquor also contains the oxidation product ammonium thiosulfate.

EXAMPLES 5-7

Various alcohols are used as solvents in the following examples. 0.2 mol of diphenylthiourea, 130 g of the alcohol, 0.1 mmol of $Cu(OAc)_2$, and ammonia are reacted with oxygen. The reaction temperature is 50° C., and the $O_2$ pressure 3 bar. The other experimental conditions and diphenyl-guanidine yields are listed in Table 1.

TABLE 1

| Example No. | Alcohol | $NH_3$ (mol) | Reaction time (min) | DPG yield (% of theor.) |
|---|---|---|---|---|
| 5 | Methanol | 2.0 | 65 | 94.5 |
| 6 | Ethanol | 1.9 | 55 | 93.8 |
| 7 | Isopropanol | 1.7 | 80 | 91.0 |

EXAMPLE 8

A reaction mixture consisting of 0.15 mol of diphenylthiourea, 130 g of toluene, 0.1 mmol of $Cu(OAc)_2$, and 0.4 mol of ammonia is reacted with oxygen (3 bar) at 50° C. During the reaction, an additional 0.3 mol of ammonia is added to the reaction mixture. The reaction time is 8.5 hours. The diphenylguanidine yield is 82% of the theoretical.

EXAMPLES 9-12

Water-methanol mixtures are used as the solvent (130 g) in the following examples. In each case, 0.1 mol of diphenylthiourea, 2.6 mol of ammonia, and 0.1 mmol of $Cu(OAc)_2$ are reacted with oxygen at 50° C. The other experimental conditions and diphenylguanidine yields are shown in Table 2.

TABLE 2

| Example No. | Weight ratio H2O:MeOH | $O_2$ pressure (bar) | Reaction time (min) | DPG yield (% of theor.) |
|---|---|---|---|---|
| 9 | 90:10 | 3 | 240 | 98.7 |
| 10 | 80:20 | 3 | 190 | 96.8 |
| 11 | 50:50 | 1 | 25 | 98.0 |
| 12 | 20:80 | 1 | 20 | 97.1 |

EXAMPLES 13-15

The amount of ammonia is varied in the following examples. 0.2 mol of diphenylthiourea and ammonia together with 75 g of water, 75 g of methanol, and 0.1 mmol of $Cu(OAc)_2$ are reacted with oxygen (1.5 bar). The other experimental conditions and diphenylguanidine yields are shown in Table 3.

TABLE 3

| Example No. | $NH_3$ (mol) | Reaction temperature (°C.) | Reaction time (min) | DPG yield (% of theor.) |
|---|---|---|---|---|
| 13 | 2.56 | 50 | 40 | 97.4 |
| 14 | 1.0 | 40 | 180 | 96.2 |
| 15 | 0.66 | 50 | 125 | 95.6 |

EXAMPLES 16-18

Other copper derivatives (0.5 mmol in each case) are used as catalysts in the following examples. In each case, 0.2 mol of diphenylthiourea, 75 g of methanol, 75 g of water, and 2.6 mol of ammonia are reacted with the catalyst and oxygen. The reaction temperature is 50° C. The other experimental conditions and product yields are shown in Table 4.

TABLE 4

| Example No. | Catalyst | $O_2$ pressure (bar) | Reaction time (min) | DPG yield (% of theor.) |
|---|---|---|---|---|
| 16 | Copper I oxide | 1.8 | 60 | 96.1 |
| 17 | Copper I chloride | 1.5 | 40 | 93.7 |
| 18 | Copper (powder) | 2.0 | 55 | 97.2 |

EXAMPLES 19-21

0.2 mol of diphenylthiourea, 75 g of methanol, 75 g of water, and 2.6 mol of ammonia are reacted at 50° C. with oxygen (1.5 bar), during which different amounts of $Cu(OAc)_2$ are employed. The other experimental conditions and diphenyl-guanidine yields are listed in Table 5.

TABLE 5

| Example No. | $Cu(OAc)_2$ (mmol) | Reaction time (min) | DPG yield (% of theor.) |
|---|---|---|---|
| 19 | 0.025 | 95 | 95.0 |
| 20 | 0.012 | 70 | 96.8 |
| 21 | 0.005 | 135 | 91.6 |

EXAMPLE 22

0.1 mol of diphenylthiourea, 130 g of water, 2.5 mol of ammonia, and 0.1 mmol of manganese II acetate as catalyst are reacted with oxygen (3 bar). The diphenylguanidine yield is 94.5% of the theoretical at a reaction temperature of 55° C. and a reaction time of 5.5 hours.

EXAMPLES 23–25

Other metal catalysts are used in the following examples. 0.2 mol of diphenylthiourea, 75 g of water, 75 g of methanol, and 2.6 mol of ammonia are reacted with the catalyst and oxygen (2 bar). The other reaction conditions and diphenylguanidine yields are listed in Table 6.

TABLE 6

| Example No. | Catalyst | (mmol) | Reaction temp. (°C.) | Reaction time (hrs) | DPG yield (% of theor.) |
|---|---|---|---|---|---|
| 23 | Co(OAc)$_2$ | (0.2) | 50 | 5.0 | 91.8 |
| 24 | Ce(NO$_3$)$_3$ | (0.2) | 60 | 4.5 | 92.4 |
| 25 | Fe(SO$_4$)$_2$ | (0.4) | 60 | 3.0 | 94.6 |

EXAMPLE 26

0.1 mol of di-o-tolylthiourea, 3 mol of ammonia, and 0.1 mmol of Cu(OAc)$_2$ are reacted in 130 g water with oxygen. The reaction temperature is 80° C. and the oxygen pressure 3 bar. Di-o-tolylguanidine is obtained in 93.2% yield after a reaction time of 3 hours.

EXAMPLE 27

To synthesize diphenylguanidine, 0.2 mol of diphenylthiourea, 2.6 mol of ammonia, and 0.1 mmol of Cu(OAc)$_2$ in a solvent mixture of 75 g of water and 75 g of methanol are reacted with oxygen. The reaction temperature is 30° C., the oxygen pressure 3.5 bar, and the reaction time 8.5 hours. The desired product is obtained with a 94.8% yield.

EXAMPLE 28

To synthesize diphenylguanidine, 0.2 mol of diphenylthiourea, 2.6 mol of ammonia, and 0.1 mmol of Cu(OAc)$_2$ in a solvent mixture of 75 g of water and 75 g of methanol are reacted with oxygen. The oxygen pressure is limited to 0.2 bar, the reaction temperature is 50° C. The product is obtained in a 92.3% yield after a reaction time of 6 hours.

EXAMPLE 29

Air is used as the oxygen-containing gas in the following example. 0.1 mol of diphenylthiourea, 1.2 mol of ammonia, and 0.02 mmol of Cu(OAc)$_2$ are reacted with air (pressure of 5 bar) in a solvent mixture of 40 g of water and 40 g of methanol. Diphenylguanidine is obtained in 94.2% yield at a reaction temperature of 50° C. and a reaction time of 70 min.

We claim:

1. A process for the preparation of an N,N'-disubstituted guanidine having the formula:

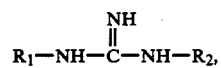

wherein R$_1$ and R$_2$ may be the same or different and represent an unsubstituted or a mono- or polysubstituted aromatic group, said process comprising reacting a corresponding N,N'-disubstituted thiourea with ammonia and oxygen or an oxygen-containing gas, in the presence of a solvent and at least one catalyst selected from the group consisting of elements with atomic numbers 21 through 30 in the Periodic Table, lanthanides, and salts, oxides, and complexes thereof.

2. The process of claim 1, wherein R$_1$ and R$_2$ represent an unsubstituted or mono- or polysubstituted phenyl group or naphthyl group, having substituent members selected from the group consisting of an alkyl group or alkoxy group having 1 to 6 carbon atoms, a cycloalkyl group, a phenyl group, a phenylether group, a benzyl group, a nitro group and a chlorine atom.

3. The process of claim 2, wherein R$_1$ and R$_2$ are a phenyl or o-tolyl group.

4. The process of claim 1, wherein at least 2 moles of ammonia are used per mole of thiourea.

5. The process of claim 1, wherein at least one of water and an organic solvent is used as a solvent.

6. The process of claim 5, wherein at least one alcohol is used as said organic solvent.

7. The process of claim 6, wherein said alcohol has 1 to 4 carbon atoms.

8. The process of claim 1, wherein at least one of copper and manganese is used as said catalyst in a form selected from the group consisting of elemental form and salts, oxides, and complexes.

9. The process of claim 1, wherin the catalyst is present in an amount of at least 0.01 mmol per mole of thiourea.

10. The process of claim 1, wherein said process is carried out at a temperature of 20° to 100° C.

11. The process of claim 1, wherein the process is carried out under a partial oxygen pressure of 0.1 to 10 bar.

* * * * *

UNITED STATES PATENT AND TRADEMARK OFFICE
CERTIFICATE OF CORRECTION

PATENT NO. : 4,898,978
DATED : February 6, 1990
INVENTOR(S) : M. Bergfeld, L. Eisenhuth, H. Zengel It is certified that error appears in the above-identified patent and that said Letters Patent is hereby corrected as shown below:

Column 1, line 47, insert -- _____ --.

*Ar = aromatic group

Signed and Sealed this

Fifteenth Day of January, 1991

Attest:

HARRY F. MANBECK, JR.

*Attesting Officer*     *Commissioner of Patents and Trademarks*